United States Patent
Petrelli et al.

(10) Patent No.: US 12,329,724 B2
(45) Date of Patent: Jun. 17, 2025

(54) COMPOSITION BASED ON L-TRYPTOPHAN, RESVERATROL AND CROCUS SATIVUS EXTRACT FOR THE TREATMENT OF MENSTRUAL CYCLE DISORDERS

(71) Applicant: KOLINPHARMA S.P.A., Milan (IT)

(72) Inventors: Rita Paola Petrelli, Milan (IT); Emanuele Lusenti, Milan (IT); Francesca Trotta, Milan (IT); Francesco Cappitelli, Milan (IT)

(73) Assignee: KOLINPHARMA S.P.A., Milan (IT)

( * ) Notice: Subject to any disclaimer, the term of this patent is extended or adjusted under 35 U.S.C. 154(b) by 894 days.

(21) Appl. No.: 17/413,907

(22) PCT Filed: Dec. 20, 2019

(86) PCT No.: PCT/IB2019/061190
§ 371 (c)(1),
(2) Date: Jun. 14, 2021

(87) PCT Pub. No.: WO2020/129003
PCT Pub. Date: Jun. 25, 2020

(65) Prior Publication Data
US 2022/0054430 A1 Feb. 24, 2022

(30) Foreign Application Priority Data
Dec. 21, 2018 (IT) .................. 102018000020932

(51) Int. Cl.
| | | |
|---|---|---|
| *A61K 31/05* | (2006.01) | |
| *A61K 9/00* | (2006.01) | |
| *A61K 31/405* | (2006.01) | |
| *A61K 36/88* | (2006.01) | |

(52) U.S. Cl.
CPC ............ *A61K 31/05* (2013.01); *A61K 9/0053* (2013.01); *A61K 31/405* (2013.01); *A61K 36/88* (2013.01)

(58) Field of Classification Search
None
See application file for complete search history.

(56) References Cited

U.S. PATENT DOCUMENTS

| | | | | |
|---|---|---|---|---|
| 9,486,464 B2 * | 11/2016 | Piraee | ................ | A23L 33/105 |
| 2013/0022673 A1 * | 1/2013 | Jaffe | ................ | A61K 31/685 |
| | | | | 424/682 |
| 2013/0190324 A1 * | 7/2013 | Kompella | ............ | A61K 47/541 |
| | | | | 548/377.1 |
| 2019/0160133 A1 | 5/2019 | Gaudout et al. | | |

FOREIGN PATENT DOCUMENTS

| | | | | |
|---|---|---|---|---|
| EP | 2672964 A1 | 12/2013 | | |
| EP | 3335717 A1 | 6/2018 | | |
| WO | WO-2016027225 A1 * | 2/2016 | ............. | A61K 31/19 |

OTHER PUBLICATIONS

What causes menstrual irregularities? (Eunice Kennedy Shiver National Institute of Child Health and Human Development, accessed Jan. 30, 2024). (Year: 2024).*
Muszynska et al. (Natural products of relevance in the prevention and supportive treatment of depression, Psychiatria Polska 2015 Polish Psychiatric Association Pol, vol. 49, No. 3, 2015, pp. 435-453. (Year: 2015).*
Performance Lab (Making the Right Choice: Magnesium Bisglycinate vs Magnesium Glycinate, Oct. 24, 2024). (Year: 2024).*
Florez-Mendez et al., "Effect of the Consumption of Chocolate Enriched With Tryptophan and Resveratrol on Biochemical Markers and Oxidative Stress in a Healthy Population", Vitae, Revista De La Facultad De Ciencias Farmaceuticas y Alimentarias, Universidad De Antioquia col. 2019, 26(1): 8-16.
Muszynska et al., "Natural products of relevance in the prevention and supportive treatment of depression", Psychiatria Polska, 2015, 49(3): 435-453.
Agha-Hosseini et al, "*Crocus sativus* L. (saffron) in the treatment of premenstrual syndrome: a double-blind, randomised and placebo-controlled trial", BJOG: An International Journal of Obstetrics and Gynaecology, 2008, 115(4): 515-519.
Lopresti et al., "Saffron (*Crocus sativus*) for depression: a systematic review of clinical studies and examination of underlying antidepressant mechanisms of action", Human Psychopharmacology Clinical and Experimental, 2014, 29: 517-527.
Steinberg, "The Treatment of Late Luteal Phase Dysphoric Disorder", Life Sciences, 1991, 49(11): 767-802.

* cited by examiner

*Primary Examiner* — Melissa S Mercier
(74) *Attorney, Agent, or Firm* — James S. Keddie; Bozicevic, Field & Francis LLP

(57) ABSTRACT

The present invention regards a multicomponent composition comprising L-tryptophan, resveratrol, a *Crocus sativus* extract and, optionally, magnesium. The present invention also regards said composition for use in a method for the therapeutic or non-therapeutic treatment of menstrual cycle disorders.

7 Claims, No Drawings

COMPOSITION BASED ON L-TRYPTOPHAN, RESVERATROL AND CROCUS SATIVUS EXTRACT FOR THE TREATMENT OF MENSTRUAL CYCLE DISORDERS

CROSS-REFERENCE TO RELATED APPLICATIONS

This application is a § 371 national phase of International Application No. PCT/IB2019/061190, filed on Dec. 20, 2019, which claims the benefit of Italian Application No. 102018000020932, filed on Dec. 21, 2018, all of which applications are incorporated by reference herein.

The present invention regards a multicomponent composition comprising L-tryptophan, resveratrol, a *Crocus sativus* extract and, optionally, magnesium. The present invention also regards said composition for use in a method for the therapeutic or non-therapeutic treatment of menstrual cycle disorders.

The menstrual cycle is a sequence of periodic physiological changes that occurs in the female reproductive system (specifically in the uterus and ovaries) and that makes pregnancy possible. The menstrual cycle of a woman has an average duration of 28 days and is divided into three phases: the preovulatory (or follicular) phase, the ovulatory phase and the post ovulatory phase (also called luteal or lutheinic phase).

The luteal phase is the phase of about 14 days that goes from ovulation up to the arrival of the menstrual period, that is when the corpus luteum is formed, that produces progesterone to prepare the uterus for a possible pregnancy.

Menstrual cycle disorders affect about 20-40% of women of childbearing age, representing the most common health problems for women. The two main symptoms that occur during the menstrual cycle, particularly in the luteal phase, are pain, mainly pelvic and abdominal pain, and alterations of mood.

The aetiology of pelvic and/or abdominal pain (pain typical of dysmenorrhea) during the luteal phase of the menstrual cycle is still subject of debate: numerous scientific studies have identified over-production of uterine prostaglandins, especially prostaglandin F2-alpha (PGF2-alpha), as the main cause of uterine contraction and thus generation of pain. Besides PGF2-alpha, vasopressin, a hormone stimulating myometrial contraction, can also play a major role in painful etiopathogenesis.

Dysmenorrhea (or painful menstruation) is a menstrual disorder, accompanied by general or local disorders and by pain affecting the pelvic region and the abdomen. Pain may precede menstruation by several days or it may accompany the cycle.

Alterations of mood manifesting itself during the menstrual cycle (premenstrual syndrome or premenstrual dysphoric disorder) are mainly due to a dysregulation of the serotonergic system, which may lead to a number of manifestations, including anxiety, mood swings, irritability, difficulty in sleeping.

Furthermore, in the context of the present invention, menstrual cycle disorders also include amenorrhea, i.e. absence of menstrual periods, irregular menstrual cycle and a menstrual period accompanied by heavy bleeding (menorrhagia).

The products currently available on the market for the treatment of menstrual cycle disorders can be divided into two groups: products based on chasteberry (*Vitex agnus castus* L.) and products based on magnesium, often combined with vitamins of group B. These products are often ineffective or only partially effective for at least a portion of the female population affected by menstrual cycle disorders.

The technical problem addressed by the present invention lies in providing a valid solution for the effective treatment, both therapeutic and non-therapeutic, of menstrual cycle disorders and related symptoms, in particular pain and/or alteration of mood, capable of overcoming the drawbacks of the prior art yet to be solved up to date, in particular as regards resolving problems (effectiveness), both in the short term and in the long term, and/or the presence of adverse effects.

To overcome said technical problems, the present invention provides a multicomponent composition comprising, as active components, L-tryptophan, resveratrol, a *Crocus sativus* extract and, optionally, magnesium. Said composition is capable of effectively and rapidly treating menstrual cycle disorders and/or the symptoms related thereto, in particular pains and/or mood disorders typical of the luteal phase of the menstrual cycle.

Furthermore, the present invention provides a composition free of adverse effects and, at the same time, a composition which is easy to prepare, economically advantageous and easy to administer across the entire female population affected by the aforementioned disorders.

These and other objects, which will be clear from the detailed description that follows, are attained by the compositions and the mixtures of the present invention due to the technical characteristics claimed in the attached claims.

Following an intense research, the Applicant found that the administration of a composition according to the present invention to a female subject in need is capable of effectively and rapidly treating symptoms or disorders caused by or deriving from the menstrual cycle, in particular symptoms or disorders of the luteal phase of the menstrual cycle. Said therapeutic or non-therapeutic treatment activity is due to the specific combination of the active components present in the composition, such as L-tryptophan, resveratrol, *Crocus sativus* extract and, optionally, magnesium, and to their synergistic effect or increase of treatment activity with respect to the activity of the individual components. In particular, the composition of the invention acts on muscle relaxation, even at the uterine level, on the perception of pain and on the psychological sphere, improving the mood state, decreasing anxiety levels and improving sleep quality.

Forming an object of the present invention is a composition (in short composition of the invention) comprising:
(i) a mixture (in short mixture of the invention) comprising, or alternatively, consisting of (I) L-tryptophan, (II) resveratrol, (III) an extract of *Crocus sativus* (saffron) stigmas; and, optionally,
(ii) at least one food grade or pharmaceutical additive and/or excipient.

In a preferred embodiment, besides (I), (II) and (III) as defined above, the composition of the invention further comprises (IV) magnesium, preferably magnesium bisglycinate (or magnesium bisglycinate chelate).

(I) L-tryptophan (IUPAC name: (2S)-2-amino-3-(1H-indol-3-yl)propanoic acid is an essential amino acid, precursor in the synthesis of serotonin and melatonin, with positive effects both on mood state and sleep quality, as well as on raising the pain threshold.

(II) resveratrol (3,54-trihydroxystilbene); IUPAC name 5-[(E)-2-(4-hydroxyphenyl)ethenyl]benzene-1,3-diol, CAS 501-36-0) is a non-flavonoid phenol naturally produced by many plant species, primarily grapes, for defence against pathogenic agents such as bacteria or fungi. Resveratrol has antioxidant, anti-inflammatory and antithrombotic properties, as known in the literature. The resveratrol present in the composition of the invention contributes toward the regularity of the menstrual cycle and reduces menstrual pain due to its ability to mimic calcium channel blockers, reducing intracellular calcium concentration at the uterine smooth muscle and thus inhibiting uterine contraction induced by PGF2-alpha.

In a preferred embodiment, (II) resveratrol is present in the composition, together with (I), (III) and, optionally, (IV), as a *Polygonum cuspidatum* extract (Siebold & Zucc.). Preferably said *Polygonum cuspidatum* extract is a root extract, more preferably a dry root extract titrated in resveratrol in a range comprised between 80% and 99.5% with respect to the total content of the extract, preferably between 90% and 99.5%, more preferably to about 98%.

An example of *Polygonum cuspidatum* extract titrated in resveratrol which can be used in the context of the present invention is a resveratrol having the technical characteristics of the product sold under the trade name Resveratrol 98% (Quimdis s.a.s., France), as described in the experimental part.

*Polygonum cuspidatum* is a perennial herbaceous plant, belonging to the *Polygonum* genus, originating in Asia, but now also widespread in Europe. The roots of *Polygonum cuspidatum* have been widely used in traditional medicine for their multiple beneficial properties in the cardiocirculatory, gastrointestinal, oropharyngeal system. The main active component present in *Polygonum cuspidatum* is resveratrol.

Said *Polygonum cuspidatum* extract comprising resveratrol is advantageously a dry hydroalcoholic extract obtained according to standard methods known to the man skilled in the art and/or reported in the literature, with titration in resveratrol determined using the HPLC method according to standard methods known to the man skilled in the art and/or reported in the literature.

Alternatively, said (II) resveratrol present in the composition subject of the invention, together with (I), (III) and, optionally, (IV), may be a *Saccharomyces cerevisiae* fermentation, preferably titrated in resveratrol to a % comprised in a range from 70% to 99.5%, preferably from 85% to 95%, more preferably to about 90% (% by weight with respect to the total weight of the fermentation product).

An example of *Saccharomyces cerevisiae* fermentation resveratrol that can be used in the context of the present invention is a resveratrol having the technical characteristics of the product sold under the trade name of RESVERATROLO CWD 90 (Evolve), as described in the experimental part.

In an embodiment, the composition of the invention comprises: (I) L-tryptophan, (II) resveratrol in the form of dry extract of *Polygonum cuspidatum* roots titrated in resveratrol in a range comprised between 80% and 99.5% with respect to the total content of the extract, preferably between 90% and 99.5%, more preferably to about 98%, (III) an extract of *Crocus sativus* (saffron) stigmas and, optionally, (IV) magnesium, preferably magnesium bisglycinate.

*Crocus sativus* (L.), commonly called saffron, is a small perennial plant belonging to the Iridaceae family. The saffron stigma contains numerous bioactive compounds, including alpha-crocetin, crocin, picrocrocin and safranal, responsible not only for the organoleptic properties of the plant itself (colour and odour), but also for the documented biological properties. The beneficial use of saffron for the gastrointestinal well-being and the cognitive sphere is not only typical of traditional medicine, but also proven by numerous clinical studies.

The extract of *Crocus sativus* stigmas present in the composition of the invention fights the disorders of the humoral sphere that characterise the luteal phase of the menstrual cycle, including anxiety, irritability, nervous tension, insomnia, alteration of the mood state.

In a preferred embodiment, in the composition according to the invention, comprising (I), (II), (III) and, optionally, (IV), said (III) extract of *Crocus sativus* stigmas is a dry extract of *Crocus sativus* stigmas titrated in Lepticrosalides® (safranal, crocin, picrocrocin) in a range comprised between 0.5% and 15% with respect to the total content of the extract (III), preferably between 1.5% and 7%, more preferably to about 3.5%; and titrated in safranal in a range comprised between 0.5% and 10% with respect to the total content of the extract, preferably between 1% and 5%, more preferably to about 2%. Advantageously, said (III) dry extract of *Crocus sativus* stigmas is titrated in Lepticrosalides® (safranal, crocin, picrocrocin) to about 3.5% and in safranal to about 2%, with respect to the total content of the extract. By way of non-limiting example, in the composition of the invention, the product sold under the trade name of Affron® which is an extract of *Crocus sativus* (saffron) stigmas standardised by means of HPLC, with known titre of Lepticrosalides® (safranal, crocin, picrocrocin) (minimum titre 3.5%) can be used as component (III).

Said dry extract of *Crocus sativus* stigmas comprising Lepticrosalides® (safranal, crocin, picro) and safranal at the percentages defined above, present in the composition of the present invention together with (I), (II) and, optionally, (IV), is a dry hydroalcoholic extract obtained according to standard methods known to the man skilled in the art and/or reported in the literature, with titration in resveratrol determined using the HPLC method according to standard methods known to the man skilled in the art and/or reported in the literature.

In an embodiment, the composition of the invention comprises: (I) L-tryptophan; (II) resveratrol in the form of dry extract of *Polygonum cuspidatum* roots titrated in resveratrol in a range comprised between 80% and 99.5% with respect to the total content of said extract, preferably between 90% and 99.5%, more preferably to about 98%; (III) a dry extract of *Crocus sativus* stigmas titrated in Lepticrosalides® (safranal, crocin, picrocrocin) in a range comprised between 0.5% and 15% with respect to the total content of the extract, preferably between 1.5% and 7%, more preferably to about 3.5%; and titrated in safranal in a range comprised between 0.5% and 10% with respect to the total content of the extract (III), preferably between 1% and 5%, more preferably to about 2%; and, optionally, (IV) magnesium, preferably magnesium bisglycinate.

In a preferred embodiment, the composition of the invention comprises: (I) L-tryptophan, (II) resveratrol in the form of dry extract of *Polygonum cuspidatum* roots titrated in resveratrol to about 98% with respect to the total content of the extract (II), (III) dry extract of *Crocus sativus* stigmas titrated in Lepticrosalides® (safranal, crocin, picrocrocin) to about 3.5% and in safranal to about 2% with respect to the total content of extract (III), and optionally (IV) magnesium, preferably magnesium bisglycinate.

Magnesium is an essential mineral in human nutrition and performs countless functions in the body, intervening in more than 300 different biological processes. Magnesium contributes to normal muscle function, being an essential cofactor of key enzymes in the muscle contraction and decontraction process. In addition, magnesium contributes to normal psychological function, as a transmitter of nerve impulses and stimulator of the various functions of the central nervous system (CNS) and peripheral nervous system, as well as of a transmitter of the nerve impulse to the neuromuscular plaque. Lastly, magnesium contributes to the production of energy both at the level of the nervous and muscle tissue, on which it causes a decontracturing and muscle relaxant action. A deficiency thereof, due to stress, together with other factors such as for example the pharmacological treatment with proton pump inhibitors or with antacid drugs, causes tension and muscle cramps.

Preferably, the (IV) magnesium present in the composition of the invention, together with (I), (II) and (III), is chelated by two glycine molecules: the chelation applied to magnesium favours its absorption by significantly reducing the likelihood of gastrointestinal adverse effects.

Forming an object of the present invention is the composition according to the present invention comprising the active components (I), (II), (III) and, optionally, (IV) as defined above, wherein said composition is for use as a medicament.

Forming an object of the present invention is the composition according to the present invention comprising the active components (I), (II), (III) and, optionally, (IV) as defined above, wherein said composition is for use in a preventive and/or curative treatment of a menstrual cycle disorder or a symptom deriving from or related with said menstrual cycle disorder, in a subject in need, such as women in childbearing age and pre-menopausal women.

In the present invention, the composition according to the present invention, comprising (i) the mixture comprising, or alternatively, consisting of (I), (II), (III) and, optionally, (IV) as defined above, is for use in a method for the treatment of a menstrual cycle disorder or a symptom deriving from or related with said menstrual cycle disorder selected from among dysmenorrhea, pelvic pain, abdominal pain, lower back pain, muscle pain, joint pain, premenstrual syndrome, alteration of mood, mood swings, irritability, anxiety, premenstrual dysphoric disorder, depression, somnolence, difficulty in sleeping, sleep quality disorder, amenorrhea, irregular menstrual cycle, menorrhagia, abdominal bloating and weight gain;

preferably for use in a method the treatment of: dysmenorrhea, pelvic pain, abdominal pain, lower back pain, muscle pain, joint pain, amenorrhea, irregular menstrual cycle, menorrhagia and/or abdominal bloating;

preferably for use in a method for the treatment of weight gain;

or, alternatively, preferably for use in a method for the treatment of: premenstrual syndrome, alteration of mood, mood swings, irritability, anxiety, premenstrual dysphoric disorder and/or depression; or, alternatively, preferably for use in a method for the treatment of: somnolence, difficulty in sleeping and/or sleep quality disorder.

The "premenstrual syndrome" (PMS) is a set of physical and psychological symptoms with onset up to two weeks prior to menstruation (luteal phase) and usually end a few hours after onset. Premenstrual syndrome is referred to related with a combination of the following symptoms: irritability, anxiety, bad mood, depression, headache or painful and turgid breasts.

The "premenstrual dysphoric disorder" is a form of premenstrual syndrome whose manifestations are so severe that they interfere with work and social activities or relationships. Premenstrual dysphoric disorder should not be confused with premenstrual syndrome usually characterised by a longer duration and a mild or moderate impact on the social-working life. Premenstrual dysphoric disorder affects women in childbearing age including pre-menopausal women in a small proportion of cases. It is characterised by a series of psychophysical symptoms that can severely limit the social and working life. In the Diagnostic and Statistical Manual of Mental Disorders (DSM-5), the disorder is in the category of mood disorders: at least five symptoms are needed in order to perform the diagnosis. The symptoms occur in the week prior to the arrival of the menstrual period (luteal phase of the cycle) and gradually resolve as the menstrual period arrives. The symptoms of premenstrual dysphoric disorder may be psychological (such as tension, irritability, feeling out of control, emotional instability or markedly depressed mood, insomnia or increased somnolence, changes in appetite, difficulty in concentrating, decreased interest in usual activities), or physical (such as breast tension, muscle or joint pain, tiredness, abdominal bloating or weight gain).

The composition according to the present invention can be administered to subjects in need through the oral route, airways, such as intranasal route, sublingual route or rectal route. Preferably, the composition of the invention is in a pharmaceutical or food form for oral use.

The composition according to the present invention for oral use can be formulated in a liquid form, such as solution, two-phase liquid system, suspension, syrup, spray, or in a semi-solid form, such as gel, soft-gel, cream, foam, or in a solid form, such as powder, granules, microgranules, flakes, aggregates, sticks or buccal solids, tablets, effervescent tablets, capsules, suppositories, bars and equivalent forms known to the man skilled in the art. Preferably, the composition according to the present invention is for oral use formulated in solid form, more preferably in solid form of granules or powders for oral suspension, for example in mono-dose sachets (formulation units) or buccal.

The daily intake of the composition according to the invention administered to a subject in need is from 1 to 6 units of formulation, preferably from 1 to 4, more preferably from 1 to 2. For example, the composition of the invention can be administered in mono-dose sachets containing powder or granules for liquid suspension in the dosage from 1 to 2 sachets per day.

In an embodiment, the composition according to the invention comprises for daily intake administered orally (in one or more formulation units) to a subject in need:
  (I) L-tryptophan at an amount comprised between 1 mg and 2000 mg, preferably between 50 mg and 1000 mg, more preferably between 100 mg and 400 mg;
  (II) resveratrol, in the form of dry root extract of *Polygonum cuspidatum* titrated in resveratrol to about 98%, at an amount comprised between 1 mg and 1000 mg, preferably between 5 mg and 200 mg, more preferably between 10 mg and 100 mg;
  (III) a dry extract of *Crocus sativus* stigmas, titrated in Lepticrosalides® (safranal, crocin, picrocrocin) to about 3.5% and titrated in safranal to about 2%, at an amount comprised between 1 mg and 1000 mg, preferably between 5 mg and 200 mg, more preferably between 10 mg and 100 mg; and, optionally,
  (IV) magnesium (magnesium element) at an amount comprised between 1 mg and 2000 mg, preferably between 50 mg and 1000 mg, more preferably between 150 mg and 500 mg.

Magnesium is present in the composition of the invention at an amount ranging from 10% to 200% of the NRV (Nutritional Reference Value) per daily intake administered through oral route to a subject in need, preferably from 50% to 150% of the NRV.

In an embodiment, the composition according to the invention comprises per formulation unit for administration through oral route (for example per sachet of granules for oral suspension) to a subject in need:

(I) L-tryptophan at a by weight amount comprised in the range from 10% to 70%, with respect to the total weight of the (i) mixture, preferably from 20% to 50%, more preferably from 30% to 40%; and at a by weight amount comprised in the range from 0.5% to 20%, with respect to the total weight of the composition ((i) mixture and (ii) additives and/or excipients), preferably from 0.5% to 15%, more preferably from 1% to 10%;

(II) resveratrol, in the form of dry extract of *Polygonum cuspidatum* roots titrated in resveratrol to about 98%, at a by weight amount comprised in the range from 1% to 40%, with respect to the total weight of the (i) mixture, preferably from 5% to 30%, more preferably from 10% to 20%; and at a by weight amount comprised in the range from 0.05% to 10%, with respect to the total weight of the composition, preferably from 0.1% to 5%, more preferably from 0.5% to 2%;

(III) a dry extract of *Crocus sativus* stigmas, titrated in Lepticrosalides® (safranal, crocin, picrocrocin) to about 3.5% and titrated in safranal to about 2%, at a by weight amount comprised in the range from 1% to 40%, with respect to the total weight of the (i) mixture, preferably from 5% to 30%, more preferably from 10% to 20%; and at a by weight amount comprised in the range from 0.05% to 10%, with respect to the total weight of the composition, preferably from 0.1% to 5%, more preferably from 0.5% to 2%; and (IV) magnesium at a by weight amount comprised in the range from 20% to 80%, with respect to the total weight of the (i) mixture, preferably from 30% to 70%, more preferably from 40% to 60%; and at a by weight amount comprised in the range from 0.5% to 20%, with respect to the total weight of the composition, preferably from 0.5% to 15%, more preferably from 1% to 10%.

Forming an object of the present invention is the non-therapeutic use of the composition according to the invention comprising the active components (I), (II), (III) and, optionally, (IV) as defined above, wherein said use is for the non-therapeutic treatment of a menstrual cycle disorder or a disorder related with the menstrual cycle, in a non-diseased subject.

Forming an object of the present invention is a method for the preventive and/or curative treatment of a menstrual cycle disorder or a symptom deriving from or related with or associated with the menstrual cycle which provides for administering the composition of the present invention at an amount effective to a subject in need, such as a woman in childbearing age or a pre-menopausal woman.

The composition of the present invention may comprise (ii) at least one pharmaceutical or food grade additive and/or excipient, that is, a substance without any therapeutic activity suitable for pharmaceutical or food use. In the context of the present invention the acceptable ingredients for pharmaceutical or food use comprise all the auxiliary substances known to the man skilled in the art such as, by way of non-limiting example, diluents, solvents (including water, glycerine, ethyl alcohol), solubilisers, thickeners, sweeteners, anti-caking agents, flavour enhancers, colouring agents, lubricants, surfactants, antimicrobials, antioxidants, preservatives, pH stabilising buffers, acidifying agents and mixtures thereof. Preferably, besides the active components (I), (II), (III) and, optionally, (IV) as defined above, the composition of the present invention for oral use in solid form of powder, granules or agglomerate further comprises maltodextrins, flavours, at least one sweetener such as sucralose, at least one anti-caking agent such as silicon dioxide and at least one acidifier such as citric acid.

Besides the active components (I), (II), (III) and, optionally, (IV) of the (i) mixture as defined above and, optionally, besides (ii) additives and/or excipients, the composition according to the present invention may further comprise other active components such as, by way of non-limiting example, anti-inflammatories, antioxidants, probiotics, in particular probiotics with antioxidant effects, antacids, products for the treatment of vaginal disorders, vitamins, in particular vitamins of group B and vitamin E, mineral salts, anxiolytics, painkillers, alpha-lipoic acid, folic acid or folates.

Lastly, forming an object of the present invention is a pharmaceutical composition, a nutraceutical composition, a dietary supplement product or a food product or a food for special medical purposes or a medical device composition comprising or, alternatively, consisting of the composition of the present invention.

The expression "medical device" in the context of the present invention is used according to the meaning laid down by the Italian Legislative Decree n° 46, dated 24 Feb. 1997 or according to the new Medical Devices Regulation (UE) 2017/745 (MDR), i.e. it indicates a substance or another product, used alone or in combination, designated by the manufacturer to be used in humans for the diagnosis, prevention, control, therapy or attenuation of a disease, the product not exercising the main action, in or on the human body, for which it is designated, neither using pharmacological or immunology means nor by means of a metabolic process, but whose function can be assisted by such means.

For the sake of clarity, to achieve the object of the present invention, the active ingredients of the composition of the present invention (I), (II), (III) and, optionally, (IV) can also be administered separately (preferably in a time interval of 30 to 60 minutes) and in any order but, preferably, (I), (II), (III) and, optionally, (IV) are administered to a subject simultaneously, even more preferably in a single composition to achieve a faster effect and for ease of administration.

When the active ingredients (I), (II), (III) and, optionally, (IV) are administered in a single composition, said single composition corresponds to the composition of the present invention.

The composition according to the present invention can be for use in the treatment methods described in the present invention in human subjects or for veterinary use, by way of non-limiting example, in pet animals such as dogs or cats, or in other mammals. Preferably, the composition according to the present invention is for use in human subjects.

The expression "treatment method" in the context of the present invention is used to indicate an action, comprising the administration of a substance, or mixture of substances or combination thereof, with the aim of eliminating, reducing/decreasing or preventing a pathology or disease and its symptoms or disorders.

Unless specified otherwise, the indication that a composition "comprises" one or more components or substances means that other components or substances can be present besides the one, or the ones, indicated specifically.

Unless otherwise specified, the expression composition comprising a component at an amount "comprised in a range from x to y" is used to indicate that said component may be present in the composition at all the amounts present in said range, even if not stated, extremes of the range included.

The compositions of the present invention allow the effective therapeutic and non-therapeutic treatment of menstrual cycle disorders or of a symptom deriving from and/or related with and/or associated with said menstrual cycle disorders, in particular in the absence of major adverse effects.

Experimental Tests

Material

Composition 1 and 2 are compositions according to the invention for oral use formulated in solid form of granules or powder (sachets) according to the content of Table 1 and Table 2.

Ingredients Composition 1: Magnesium (magnesium bisglycinate chelate); L-tryptophan; dry extract (d.e.) of *Polygonum cuspidatum* root Siebold Zucc. titrated to 98% in resveratrol; dry extract of *Crocus sativus* L. stigmas, titrated to 3.5% in Lepticrosalides® (safranal, crocin, picrocrocin) and to 2% in safranal (Afton®); acidifier: citric acid anhydrous; maltodextrins; flavour; sweetener: sucralose; anticaking agent: silicon dioxide.

TABLE 1

| Nutrient | mg/daily intake (1-2 sachets) |
| --- | --- |
| Magnesium bisglycinate | 830-2780 mg |
| of which Magnesium (about 18%) | 150-500 mg |
| Tryptophan | 100-400 mg |
| *Polygonum cuspidatum* d.e. | 10.2-102 mg |
| of which Resveratrol (98%)[1] | 10-100 mg |
| *Crocus sativus* d.e. | 10-100 mg |
| of which safranal (about 2%) | 2-20 mg |
| of which Lectoprosalides ® | (approximately) |
| (about 3.5%) | 3.5-35 mg |
|  | (approximately) |
| Additives and/or excipients (various) | 1260-4520 mg |
| Total Weight | 3200-7900 mg |

[1]for example: product sold under the trade name Resveratrol 98% produced by Quimdis s.a.s. France

TABLE 2

| Nutrient | mg/daily intake (1-2 sachets) |
| --- | --- |
| Magnesium bisglycinate | 830-2780 mg |
| of which Magnesium (about 18%) | 150-500 mg |
| Tryptophan | 100-400 mg |
| *Saccharomyces cerevisiae* fermentation | 10.2-102 mg |
| resveratrol (90%)[2] | 10-100 mg |
| *Crocus sativus* d.e. | 10-100 mg |
| of which safranal (about 2%) | 2-20 mg |
| of which Lectoprosalides ® | (approximately) |
| (about 3.5%) | 3.5-35 mg |
|  | (approximately) |
| Additives and/or excipients (various) | 1260-4520 mg |
| Total Weight | 3200-7900 mg |

[2]for example: product sold under the trade name RESVERATROLO CWD 90 produced by Evolva Resveratrol 98% produced by Quimdis s.a.s. France, such as resveratrol extracted from *Polygunum cuspidatum*, has the following technical features: CAS N° 501-36-0; Grain size: >95% passes through 80 mesh sieve; Solubility: 0.03 g/L in H2O; Density >0.40 g/ml (bulk), >0.050 g/ml (tapped); Content >98% (HPLC); Loss by drying <5% (CP); Hydroalcoholic extraction (e.g. EtOH: H2O).

RESVERATROLO CWD 90 produced by Evolva, such as *Saccharomyces cerevisiae* fermentation resveratrol, has the following technical features: Composition: 90% from trans-resveratrol produced by fermentation and 10% of excipients; Form: powder dispersible in cold water; Dispersion: dispersion of 560 mg in 100 ml of water passes through a 720 micron screen; Titre (on the anhydrous) >90.0%; IR Identification: >90% corresponds to the internal standard; Grain size: particles <10 microns >=10.00%; Average particle size <50.00 μm; Median grain size <45 μm.

The invention claimed is:

1. A method comprising administering a composition comprising
   (i) a mixture comprising:
      (I) L-tryptophan;
      (II) resveratrol;
      (III) an extract of *Crocus sativus* stigmas;
   (ii) at least one food grade or pharmaceutical additive and/or excipient, and
   (iii) magnesium bisglycinate,
to a subject having a menstrual cycle disorder.

2. The method of claim 1, wherein the subject has dysmenorrhea, pelvic pain, abdominal pain, lower back pain, muscle pain, joint pain, amenorrhea, irregular menstrual cycle, menorrhagia, abdominal bloating and/or weight gain.

3. The method of claim 1, wherein said menstrual cycle disorder is, or comprises a symptom deriving from said menstrual cycle disorder selected from the group consisting of: alteration of mood, mood swings, irritability, anxiety, depression, premenstrual dysphoric disorder, somnolence, difficulty in sleeping, and sleep quality disorder.

4. The method of claim 1, wherein said (II) resveratrol is present in the mixture as *Polygonum cuspidatum* extract titrated in resveratrol in a range comprised between 80% and 99.5%.

5. The method of claim 1, wherein said (III) extract of *Crocus sativus* stigmas is a dry extract of stigmas titrated in safranal, crocin and picrocrocin in a range comprised between 0.5% and 15% with respect to the total content of the extract (III); and titrated in safranal in a range comprised between 0.5% and 10% with respect to the total content of the extract (III).

6. The method of claim 1, wherein said composition is formulated in solid form for oral use.

7. The method of claim 1, wherein said composition comprises for daily intake in solid form for oral use:
   (I) L-tryptophan at an amount comprised between 1 mg and 2000 mg;
   (II) resveratrol, in the form of dry root extract of *Polygonum cuspidatum* titrated in resveratrol to about 98%, at an amount comprised between 1 mg and 1000 mg;
   (III) a dry extract of *Crocus sativus* stigmas, titrated in safranal, crocin and picrocrocin to about 3.5% and titrated in safranal to about 2%, at an amount comprised between 1 mg and 1000 mg; and
   (IV) magnesium (magnesium element) at an amount comprised between 1 mg and 2000 mg.

* * * * *